(12) United States Patent  
Pusch

(10) Patent No.: US 8,464,597 B2
(45) Date of Patent: Jun. 18, 2013

(54) SENSOR ASSEMBLY FOR MEASURING FORCES AND/OR TORQUES AND USE OF SAID ASSEMBLY

(75) Inventor: Martin Pusch, Duderstadt (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 383 days.

(21) Appl. No.: 12/091,854

(22) PCT Filed: Oct. 12, 2006

(86) PCT No.: PCT/DE2006/001791
§ 371 (c)(1),
(2), (4) Date: Apr. 28, 2008

(87) PCT Pub. No.: WO2007/048375
PCT Pub. Date: May 3, 2007

(65) Prior Publication Data
US 2008/0276725 A1   Nov. 13, 2008

(30) Foreign Application Priority Data
Oct. 26, 2005  (DE) .......................... 10 2005 051 495

(51) Int. Cl.
*G01D 7/00*   (2006.01)
*A61B 5/103*   (2006.01)

(52) U.S. Cl.
USPC ..................... 73/862.041; 600/595

(58) Field of Classification Search
USPC ..................... 73/862.041–862.046
See application file for complete search history.

(56) References Cited

U.S. PATENT DOCUMENTS 4,488,441 A  * 12/1984 Ramming ................ 73/862.044
4,640,138 A    2/1987  Meyer et al.
4,849,730 A  *  7/1989 Izumi et al. ...................... 338/2

(Continued)

FOREIGN PATENT DOCUMENTS

DE   EP0575634    * 12/1993
DE   4412377 A1   4/1994
DE   3701372 A1   1/1997
DE   10013059 A1  3/2000

(Continued)

OTHER PUBLICATIONS

International Search Report for PCT/DE2006/001791 mailing date Feb. 3, 2007, 3 pgs.

*Primary Examiner* — Andre Allen
*Assistant Examiner* — Octavia Davis-Hollington
(74) *Attorney, Agent, or Firm* — Holland and Hart LLP

(57) ABSTRACT

A sensor assembly is provided for measuring forces and/or torques which are transmitted by means of a rigid transmitter having a first part and a second part. The sensor assembly includes a first connection, a second connection, electromechanical sensor elements, a first flange, a second flange and a plurality of struts. The first and second connections are connectable to the first and second parts of the transmitter, respectively. The electromechanical sensor elements convert mechanical parameters into electrical parameters. The first flange surrounds the first connection and originates at the first connection. The second flange is aligned substantially parallel to the first flange. The second connection is arranged on the second flange and has a first surface and a second surface. The plurality of struts are substantially perpendicular to the first flange and connect the first flange to the second flange. A gap is formed between the first flange, the second flange and the struts, and is larger than a width of the struts. The electromechanical sensor elements are designed for determining strains or compressions and are arranged next to the plurality of struts on at least one of the first and second surfaces of the second flange.

24 Claims, 3 Drawing Sheets

U.S. PATENT DOCUMENTS

| | | | | |
|---|---|---|---|---|
| 5,490,427 | A * | 2/1996 | Yee et al. | 73/767 |
| 6,105,438 | A * | 8/2000 | Gieseke | 73/862.042 |
| 6,269,702 | B1 * | 8/2001 | Lambson | 73/862.045 |
| 6,918,308 | B2 * | 7/2005 | Biedermann et al. | 73/862.629 |
| 7,500,407 | B2 * | 3/2009 | Boiten | 73/862.191 |

FOREIGN PATENT DOCUMENTS

| | | |
|---|---|---|
| DE | 10139333 A1 | 3/2003 |
| EP | 1559384 | 8/2005 |
| WO | 2004/111592 A1 | 6/2004 |

\* cited by examiner

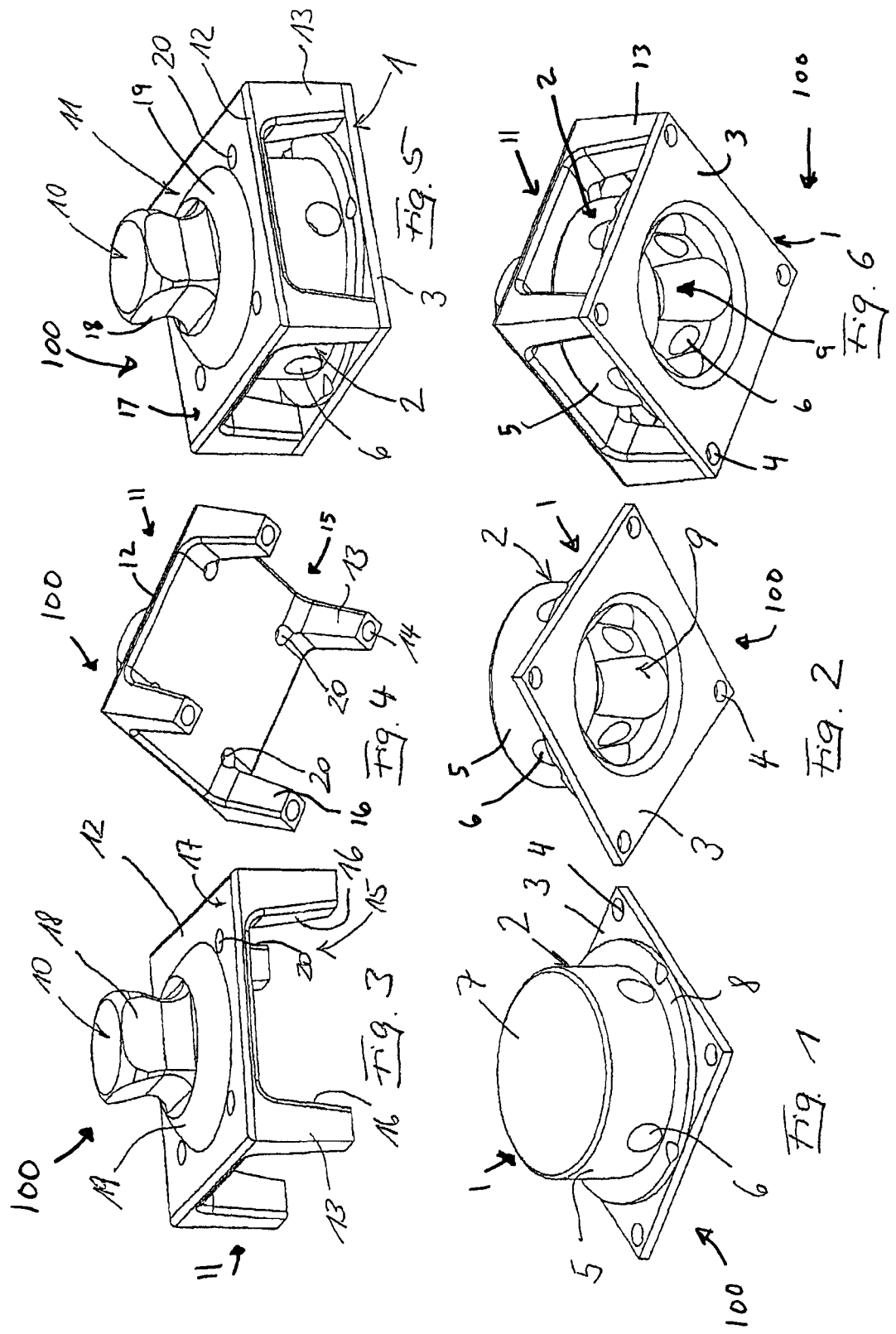

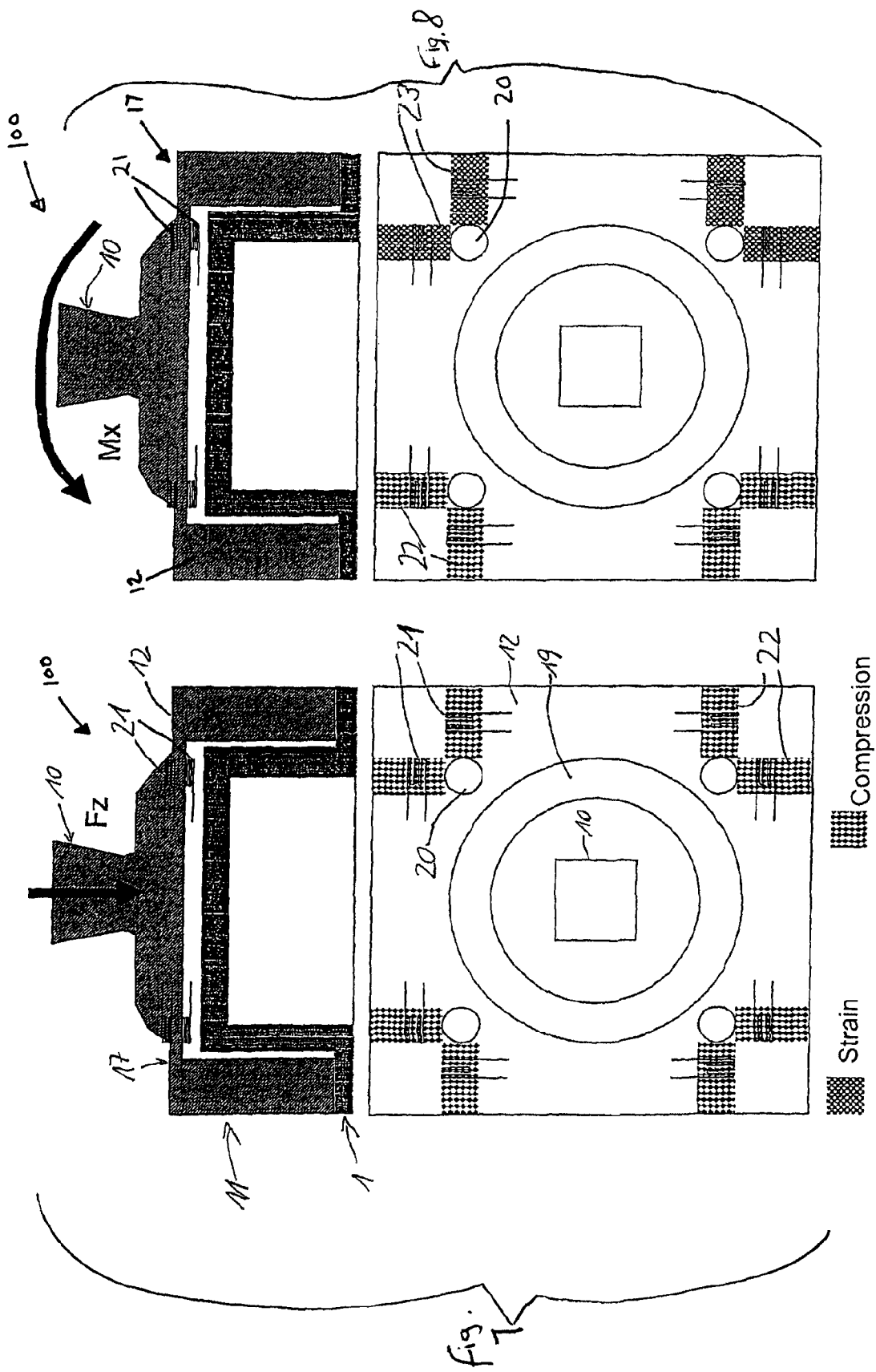

SENSOR ASSEMBLY FOR MEASURING FORCES AND/OR TORQUES AND USE OF SAID ASSEMBLY

CROSS-REFERENCE TO RELATED APPLICATION

This patent application is a national stage application of International Application No. PCT/DE2006/001791 filed Oct. 12, 2006, which claims priority to German Application No. 10 2005 051 495.2, filed on Oct. 26, 2005. The entire content of these applications are hereby expressly incorporated by reference.

TECHNICAL FIELD

The invention relates to a sensor assembly for measuring forces and/or torques which are transmitted by means of a rigid transmitter, the sensor assembly being able to be connected to a first part of the transmitter by means of a first connection and to a second part of the transmitter by means of a second connection, and the sensor assembly being provided with electromechanical sensor elements for converting mechanical parameters into electrical parameters.

The invention further relates to a use of such a sensor assembly in an artificial limb, in particular in an artificial leg.

BACKGROUND

Sensor assemblies, by means of which a gait analysis of a patient is to be carried out, are known. Because the sensor assemblies have a very large volume, they must be installed into test prostheses which should correspond as closely as possible to the prostheses used in practice. However, due to the different construction of the test prosthesis and the changed weight distribution due to the sensor assembly, the only gait analyses possible may correspond only in a very limited manner to the gait with a prosthesis used in practice.

Furthermore, there have been attempts to provide the patient with a sensor assembly, constructed with accelerometers, on an extremity fitted with the prosthesis. Such an assembly can be used to analyze the gait dynamics, but it allows no measurement of loads on the prosthesis in a stationary state or in the case of quasi-static movements.

DE 101 39 333 A1 discloses a prosthesis with a thigh part, a knee joint, a lower leg part and a foot part, in which the lower leg part is formed to hold a sensor assembly. The sensor assembly is set up for the metrological separation of axial loads from bending loads. It includes a frame with bent side-struts for measuring the bending load and a central, thin strut for measuring the vertical (axial) load.

It is not only desirable to determine forces and/or torques for prostheses, but also for numerous other areas of application, for example for the design and control of robot arms.

SUMMARY

The present invention is therefore a sensor assembly of the type mentioned initially which can be constructed in a small space and which permits a reliable measurement of static and dynamic loads.

In accordance with the invention, a sensor assembly of the type mentioned initially has a first flange which surrounds the first connection, originates at the first connection, and is connected to a second flange via struts which are perpendicular to the first flange. The second flange is aligned parallel to the first flange. A gap between the struts is larger than a width of the struts. The second connection is arranged on the second flange. The sensor elements are designed for determining strains or compressions and are arranged next to the struts on at least one of the two surfaces of the second flange.

The inventive sensor assembly allows safe transmission of the forces from the first connection to the second connection, which is preferably arranged centrally on the second flange, and vice versa, with the transmitted forces being recognizable by measuring very slight deformations on the second flange. Due to the transmission of the forces between the two flanges by means of the struts, the deformations are concentrated in the regions of the surface of the second flange adjacent to the struts and can be detected there by the sensor elements which react to strain or compression. The struts, whose length preferably exceeds their width, bring about a decoupling of the two flanges, which permits a transmission of forces and on the other hand concentrates the deformations onto one of the flanges, in this case onto the second flange, so that a decoupling of the two flanges with respect to the deformations, that is to say with respect to the measuring effect, is achieved.

In a preferred embodiment of the invention, the sensor elements for recording strains and compressions are arranged on both surfaces of the second flange. By differentiating between strains and compressions, the type of transmitted forces and/or torques can be determined more reliably. Furthermore, it is possible to obtain increased measurement signals if the sensor elements located on the top side and on the underside of the second flange are interconnected in a suitable manner.

In a preferred embodiment of the invention, the sensor assembly is constructed in two parts with a first part having the first flange and a second part having the second flange and the struts, the two parts being able to be rigidly connected to one another, for example by a screw connection. The screw connection can preferably be carried out via the struts, if these are provided with a threaded bore for holding a fixing screw.

The first connection of the sensor assembly is preferably formed in the shape of a hat with a cylindrical cross section, to which the first flange adjoins. The hat-shaped connection can preferably engage over a known adjustment pyramid and can be provided with threaded through-bores for adjustment screws which engage on the faces of the adjustment pyramid.

By way of example, the second connection can be formed with an adjustment pyramid which merges into the second flange with a convex bulge.

Preferably, the sensor elements are strain gauges which, in a preferred embodiment of the invention, are positioned to record linear strains or compressions.

The arrangement of recesses can influence the position of the preferably linear strain or compression regions on the second flange. The recesses can be circular bores or else through-openings with an arbitrary outer contour, for instance a triangular outer contour.

Preferably, the first and the second flange have a quadrangular contour, and four struts are provided to connect the two flanges at their corners. The recesses which are provided to position the strain or compression regions in the second flange are preferably located between the second connection and the struts, that is to say in a diagonal direction of the preferably quadratic second flange.

Such a construction allows the formation of linear strain or compression regions parallel to the edges of the second flange, originating at the recesses and running parallel to the edges of the second flange, so the strain gauges are positioned for this purpose.

The inventive sensor assembly can be implemented in a very small space and requires an overall height of not more than about 2 to 3 cm.

By way of example, the inventive sensor assembly can thus be adapted to the size and the weight of a rotation adaptor which is arranged directly above the artificial knee joint in a leg prosthesis. The rotation adaptor of such a prosthesis, which makes an additional rotation possible, can easily be exchanged with the inventive sensor assembly so that the forces and torques required for gait analysis can be determined on the prosthesis constructed for subsequent use by the patient. The determination of the loads can thus be undertaken on the final prosthesis, with optimization being possible by adjusting the prosthesis.

The inventive sensor assembly is also suited for long-term installation in a prosthesis in order to carry out long-term investigations.

BRIEF DESCRIPTION OF THE DRAWINGS

In the following text, the invention is explained in more detail with reference to an exemplary embodiment illustrated in the drawings, in which FIG. 1 shows a perspective side view of a first part of a sensor assembly;

FIG. 2 shows a perspective view, from diagonally below, of the first part in accordance with FIG. 1;

FIG. 3 shows a perspective side view of a second part of the sensor assembly;

FIG. 4 shows a perspective view, from diagonally below, of the second part in accordance with FIG. 3;

FIG. 5 shows a perspective side view of the sensor assembly assembled from both parts;

FIG. 6 shows a perspective view, from diagonally below, of the sensor assembly in accordance with FIG. 5;

FIG. 7 shows a schematic sectional view of the sensor assembly for an axial load (z-direction) with a schematic illustration of linear compression regions on a second flange;

FIG. 8 shows an illustration in accordance with FIG. 7 for a torque about a horizontal axis (x-axis);

DETAILED DESCRIPTION

Figure 10:
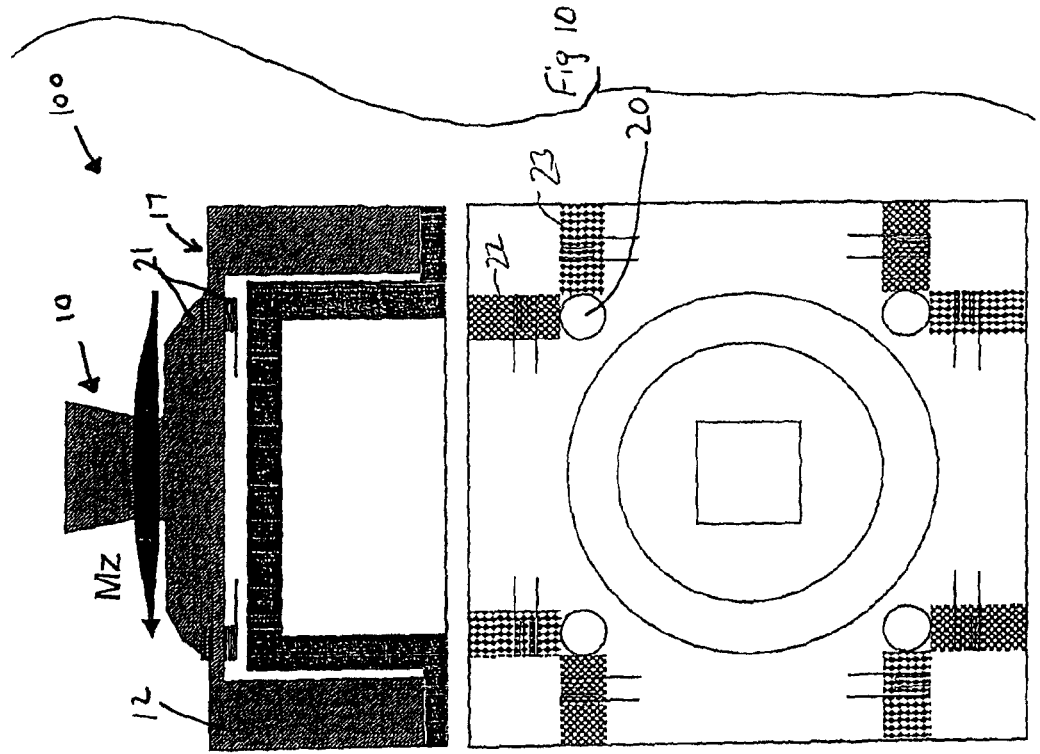
FIG. 10 shows a schematic illustration in accordance with FIG. 7 for a torque about a vertical axis (z-axis).

FIGS. 1 to 6 show a construction of an exemplary embodiment of an inventive sensor assembly 100 including a first part 1, which is constructed from a hat-shaped cylindrical connection 2 and an adjoining quadratic flange 3. The quadratic flange 3 has through-holes 4 for fixing screws (not illustrated) at its corners.

The hat-shaped cylindrical connection 2 is constructed with a cylindrical lateral wall 5, in which threaded bores 6 are located, separated in each case by an angle of rotation of about 90°. The hat-shaped cylindrical connection 2 has a circular-cylindrical bottom 7 on its top side and an annular brim 8 on its underside, the annular brim 8 being integrally connected to the quadratic flange 3 and strengthening it.

FIG. 2 shows that the hat-shaped cylindrical connection 2 has an approximately rectangular holding space 9, which serves for holding an adjustment adaptor 10 (FIG. 3) which has four inclined adjustment surfaces, against which the adjustment screws, which have been screwed through the threaded bores 6, press.

The adjustment adaptor 10 is formed on a second part 11 of the sensor assembly 100. The second part 11 has a second quadratic flange 12, the dimensions of which correspond to the dimensions of the first quadratic flange 3. The two quadratic flanges 3, 12 are connected to one another by struts 13 which are integrally formed on the second part 11 and which extend downward at the corners of the second quadratic flange 12, so that the struts 13 bear on the first quadratic flange 3, radially outside of the hat-shaped cylindrical connection 2. In each case, the struts 13 are provided with a threaded blind hole 14 on their underside which can be aligned with the through-holes 4 of the first quadratic flange 3.

It can be seen from FIGS. 3 and 4 that the struts 13 have a rectangular cross section and taper off toward their free ends, that is to say downward, by means of an incline 16, which points toward a gap 15 between two struts 13.

The adjustment adaptor 10 is located on a top side 17 of the second quadratic flange 12, which is facing away from the struts 13. It is formed in a known manner in the form of an upside-down pyramidal frustum and thus has four inclined planar adjustment surfaces 18 which can interact with adjustment screws for the purpose of adjustment. The adjustment adaptor 10 merges into a base 19 with an enlarged diameter which creates a transition to the second quadratic flange 12 by means of a bulging plane.

The adjustment adaptor 10 forms a second connection of the sensor assembly 100. In each case, a recess 20 in the form of a through-bore is located between this second connection and the struts 13, which are arranged in the corners of the second quadratic flange 12, and hence in the diagonal direction of the second quadratic flange 12, the recess 20 influencing the formation of stress or strain regions, which is described in more detail below.

FIGS. 5 and 6 show the sensor assembly 100 assembled from the two parts 1, 11 in the assembled state (but without fixing screws). It can be seen that between the holding space 9 of the first connection and the adjustment adaptor 10 forming the second connection, only a small overall height of about 2 to 3 centimeters is required.

FIGS. 7 to 10 in each case schematically show a vertical section through the sensor assembly 100 in accordance with FIGS. 1 to 6, with, however, a schematic illustration of strain gauges 21 adhered to both surfaces of the second quadratic flange 12 as sensor elements.

The plan view located below in each case in FIGS. 7 to 10 shows the positioning of the strain gauges 21 such that their length changes by linear compression regions 22 or strain regions 23, resulting in a changed resistance.

FIG. 7 shows the case of force acting in the z-direction, that is to say in the axial direction of a tubular skeletal prosthesis for a lower leg. The strain gauges 21, located on the top side 17 of the second quadratic flange 12, are in this case located in compression regions 22 which in each case extend in linear fashion, parallel to the edges of the second quadratic flange 12, from the recesses 20 to the adjacent edge. The accordingly aligned strain gauges 21 thus change their resistance value in the direction of compression.

In accordance with FIG. 8, the adjustment adaptor 10 is acted upon by torque about an axis perpendicular to the plane of the drawing (x-direction). For the strain gauges 21 located on the top side 17 of the second quadratic flange 12, the torque leads to compression on the side to which the torque is directed (compare the plotted arrow Mx in FIG. 8), whereas it leads to the formation of strain regions 23 on the opposite side.

Figure 9:
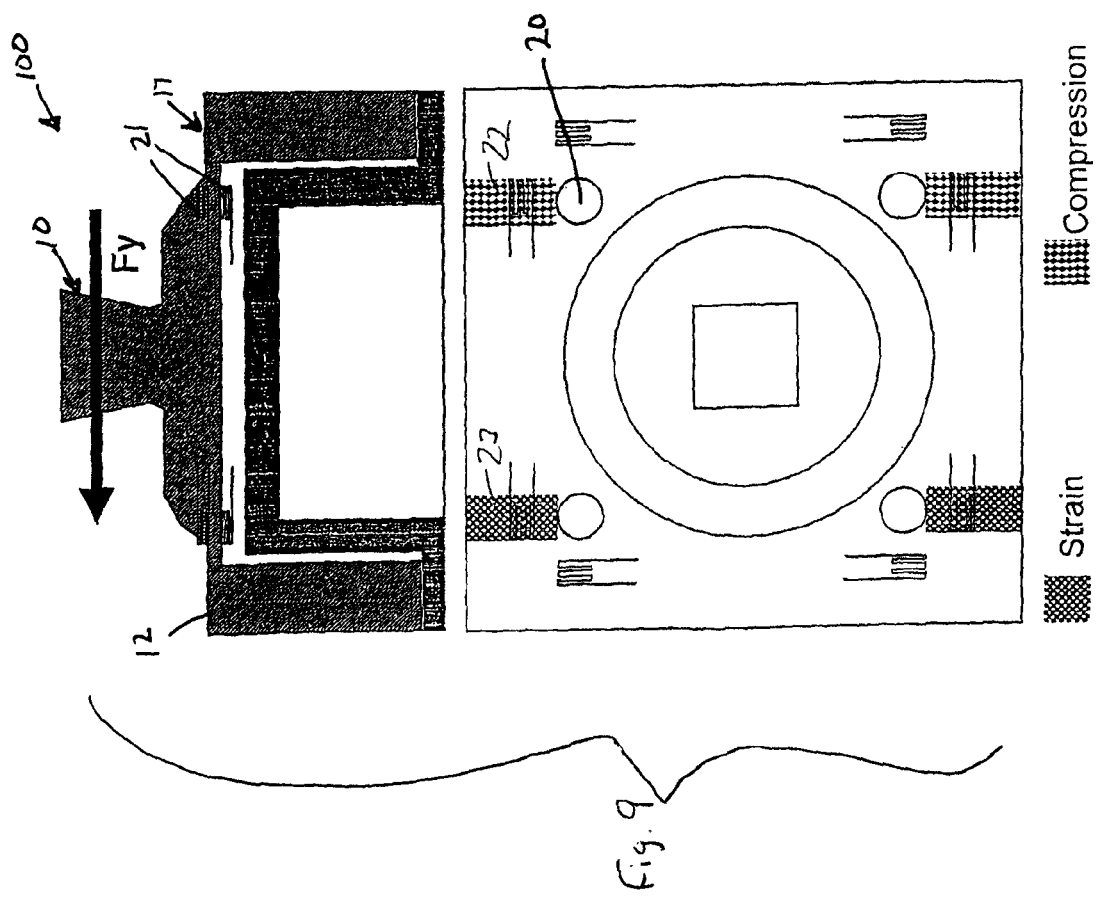
FIG. 9 shows a schematic illustration in accordance with FIG. 7 for an acting lateral force.

FIG. 9 shows a lateral force acting on the adjustment adaptor 10 in the plane of the drawing (y-direction), by means of which strain regions 23 and compression regions 22 are formed only perpendicular to the acting force, while the remaining strain gauges 21 on the top side 17 of the second quadratic flange 12 remain without a measurement signal.

In the case of torque Mz acting in the z-direction illustrated in FIG. 10, a compression region 23 and a strain region 22 are created at each recess 20, with the compression region 23 leading the strain region 22 in each case by 90°, as seen in the direction of the torque Mz.

From the illustrated examples, it can be seen that the different forces and moments that occur can be detected using the strain gauges 21 as sensor elements.

The strain gauges 21 on the underside of the second quadratic flange 12 in each case yield signals that are complementary to the signals of the strain gauges 21 on the top side 17 of the second quadratic flange 12, so that these can contribute to an amplified measurement signal in the case of a suitable addition.

The invention claimed is:

1. A sensor assembly in an artificial leg for measuring forces and torques for gait analysis, the forces and torque being transmitted by means of a rigid transmitter having a first part and a second part, the sensor assembly comprising:
    a first connection connectable to the first part of the transmitter;
    a second connection connectable to the second part of the transmitter;
    electromechanical sensor elements for converting mechanical parameters into electrical parameters;
    a first flange surrounding the first connection and originating at the first connection;
    a second flange aligned substantially parallel to the first flange, wherein the second connection is arranged on the second flange and has a first surface and a second surface;
    a plurality of struts substantially perpendicular to the first flange and connecting the first flange to the second flange, the plurality of struts transmitting forces from the first flange to the second flange;
    wherein a gap is formed between the first flange, the second flange and the struts, and wherein the gap between the struts is larger than a width of the struts; and
    wherein the electromechanical sensor elements are designed for determining strains or compressions and are arranged next to the plurality of struts on at least one of the first and second surfaces of the second flange;
    wherein the sensor assembly has an x-direction, a y-direction, and a z-direction that are perpendicular to each other, and strains and compressions of the electromechanical sensor elements are used to determine different forces and moments occurring in at least two of the directions of the sensor assembly for use in the gait analysis.

2. The sensor assembly of claim 1, wherein the electromechanical sensor elements for recording strains or compressions are arranged on the first and second surfaces of the second flange.

3. The sensor assembly of claim 1, further comprising:
    a first part including the first flange; and
    a second part including the second flange;
    wherein the sensor assembly is constructed from the first and second parts and wherein the first and second parts are rigidly connectable to one another.

4. The sensor assembly of claim 1, wherein each of the plurality of struts include a threaded bore for holding a fixing screw.

5. The sensor assembly of claim 1, wherein the first connection is formed having a shape of a hat with a cylindrical cross section to which the first flange adjoins.

6. The sensor assembly of claim 1, wherein the second connection merges into the second flange with a convex bulge.

7. The sensor assembly of claim 1, wherein the electromechanical sensor elements comprise strain gauges.

8. The sensor assembly of claim 7, wherein the strain gauges are positioned to record linear strains or compressions.

9. The sensor assembly of claim 7, wherein the strain gauges are positioned to record strains or compressions from recesses arranged between the second connection and the plurality of struts, wherein the strains or compressions run parallel to the edges of the second flange.

10. The sensor assembly of claim 1, wherein the second flange has recesses for positioning strain regions and compression regions.

11. The sensor assembly of claim 1, wherein the first flange and the second flange have a quadrangular contour with a plurality of corners, and the struts connect the first and second flanges together at the plurality of corners.

12. The sensor assembly of claim 1, wherein the plurality of struts includes four struts.

13. The sensor assembly of claim 1, further comprising recesses arranged diagonally between the second connection and the plurality of struts.

14. The sensor assembly of claim 1, wherein the second connection is arranged substantially centrally with respect to the second flange.

15. The sensor assembly of claim 1, wherein the sensor assembly is used in an artificial limb in place of a removable component of the artificial limb and wherein the sensor assembly is adapted to dimensions of the removable component.

16. The sensor assembly of claim 15, wherein the artificial limb is in an artificial leg.

17. The sensor assembly of claim 15, wherein the removable component is a rotation adaptor.

18. A sensor assembly configured to measure forces and torques in an artificial leg for use in gait analysis, the sensor assembly comprising:
    a connection member configured to connect a first portion of the prosthetic device to the sensor assembly;
    an adapter member configured to connect a second portion of the prosthetic device to the sensor assembly;
    a first flange extending from the connection member;
    a second flange extending from the adapter member and arranged substantially parallel with and spaced apart from the first flange;
    a plurality of struts extending from the first flange and connecting the first flange to the second flange, the plurality of struts transmitting forces from the first flange to the second flange;
    at least one electromechanical sensor element configured to determine strains or compressions, the at least one electromechanical sensor element being arranged on the second flange next to the plurality of struts;
    wherein the sensor assembly has an x-direction, a y-direction, and a z-direction that are perpendicular to each other, and strains and compressions of the at least one electromechanical sensor element are used to determine different forces and moments occurring in at least two of the directions of the sensor assembly for use in the gait analysis.

19. The sensor assembly of claim 18, wherein the at least one electromechanical sensor element includes a plurality of electromechanical sensor elements.

20. The sensor assembly of claim 18, wherein the at least one electromechanical sensor element is positioned on a surface of the second flange that is arranged perpendicular to the plurality of struts.

21. The sensor assembly of claim 18, wherein the second flange and the plurality of struts are integrally formed as a single piece.

22. The sensor assembly of claim 18, wherein a plurality of electromechanical sensor elements are positioned on the second flange next to each of the plurality of struts.

23. The sensor assembly of claim 18, wherein a plurality of electromechanical sensor elements are positioned on opposing sides of the second flange.

24. The sensor assembly of claim 18, wherein the struts are positioned radially outward from the connection member and adapter member.

* * * * *